United States Patent [19]
Jensen et al.

[11] 3,994,027
[45] Nov. 30, 1976

[54] PREPUPILLARY LENS FOR IMPLANTING IN A HUMAN EYE

[75] Inventors: Ronald P. Jensen, Baldwin Parks; James Fetz, Los Angeles, both of Calif.

[73] Assignee: California Intraocular Lens Corporation, Baldwin Parks, Calif.

[22] Filed: May 28, 1975
(Under Rule 47)

[21] Appl. No.: 581,539

[52] U.S. Cl. ............................................. 3/13
[51] Int. Cl.² ............................ A61F 1/16; A61F 1/24
[58] Field of Search .......................................... 3/13, 1

[56] References Cited
UNITED STATES PATENTS

| | | |
|---|---|---|
| 2,834,023 | 5/1958 | Lieb .............................................. 3/1 |
| 3,922,728 | 12/1975 | Krasnov ...................................... 3/13 |

OTHER PUBLICATIONS
"The Iridocapsular (Two-Loop) Lens and the Iris-- Clip (Four-Loop) Lens in Pseudophakia" by C. D. Binkhorst, Transactions of the American Academy of Ophthalmology, vol. 77, Sept.–Oct. 1973, pp. 589–617.

*Primary Examiner*—Ronald L. Frinks
*Attorney, Agent, or Firm*—W. Edward Johansen

[57] ABSTRACT

The invention is a prepupillary lens which may be surgically implanted into a human eye. The lens may be either a two-loop lens or a four-loop lens. The two-loop lens has a convex surface and a planar surface, into which a pair of posterior loops are embedded and fused therein. The four-loop lens is similar to the two-loop lens, but it also includes two pairs of parallel bores in the lens disposed in a plane between the convex surface and the planar surface and aligned with the posterior loops and a pair of anterior loops inserted into the bores and fused therein.

6 Claims, 15 Drawing Figures

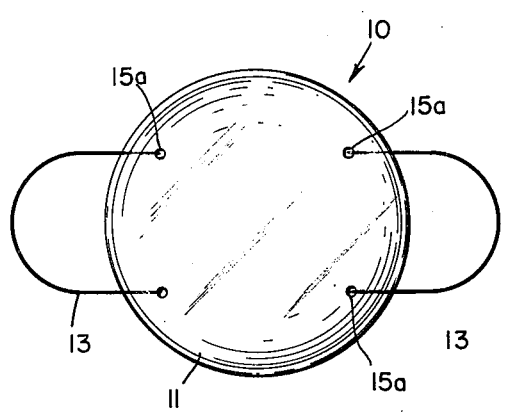
Fig. 2. PRIOR ART
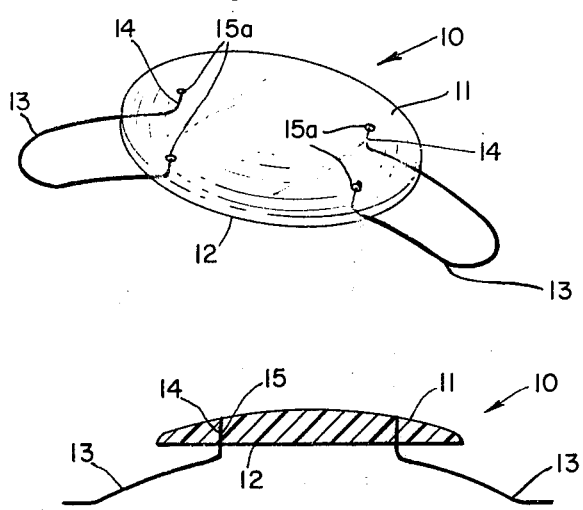
Fig. 1. PRIOR ART
Fig. 3. PRIOR ART
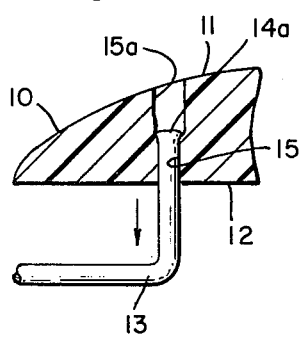
Fig. 4c. PRIOR ART
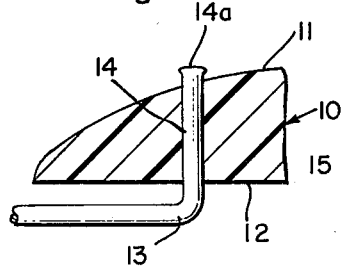
Fig. 4b. PRIOR ART
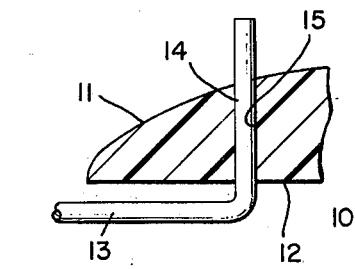
Fig. 4a PRIOR ART
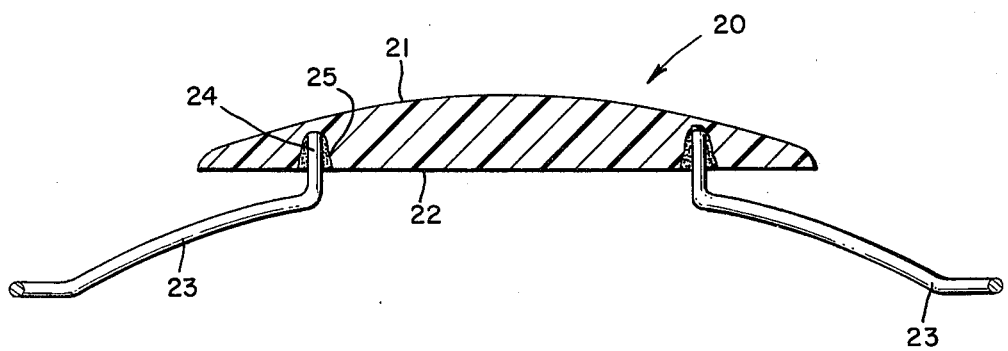
Fig. 6.

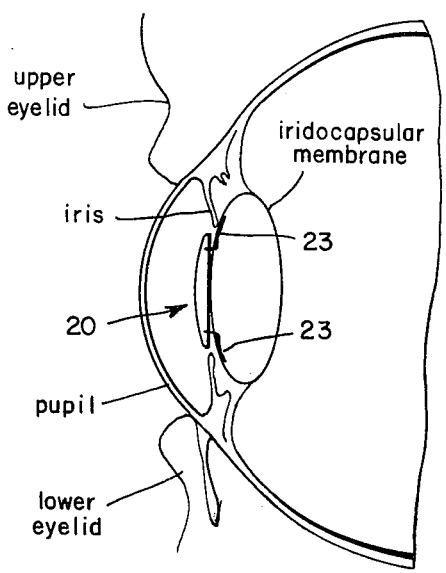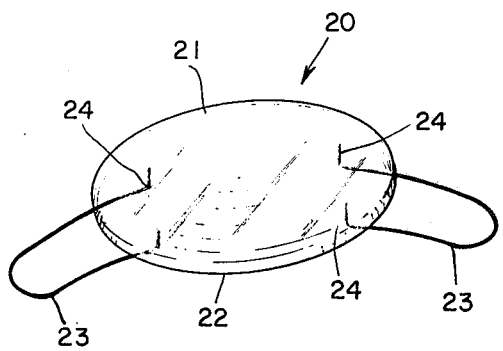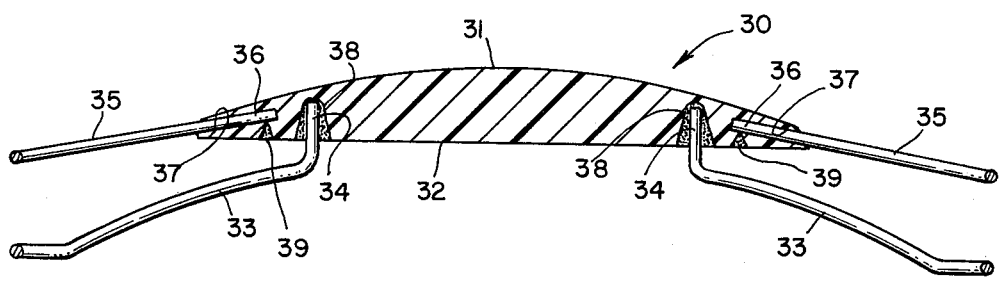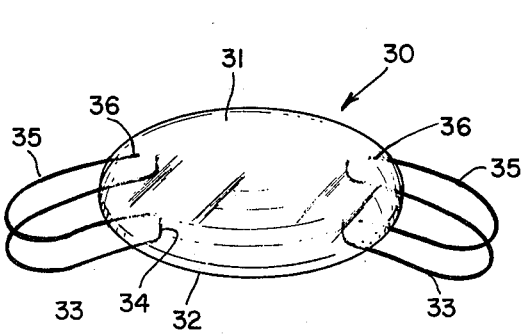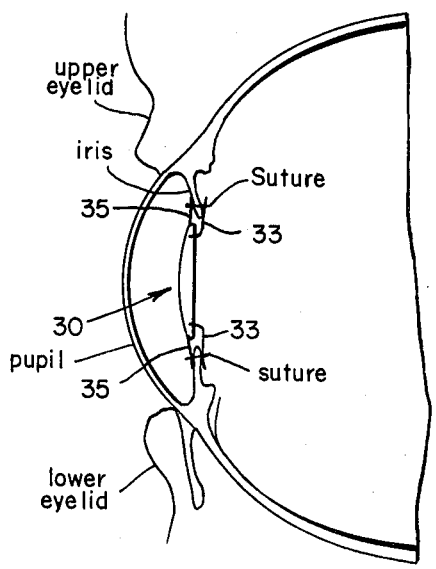

PREPUPILLARY LENS FOR IMPLANTING IN A HUMAN EYE

BACKGROUND OF THE INVENTION

1. Field of the Invention

The present invention relates to an improved prepupillary lens which may be surgically implanted in a human eye and more particularly to a method for securing on the lens loops which anchor the lens in the eye.

2. Statement of the Prior Art

In the prior art prepupillary lenses have been used in an operation for surgically implanting a lens on the iris of a human eye. Cornelius D. Binkhorst, M. D., who has performed this operation since 1958, has used a two-loop lens and a four loop lens. He has described both of these lenses in an article entitled, "The Iridocapsular (Two-loop) Lens and the Iris-clip (Four-loop) Lens in Pseudophakia", which he wrote for the 1973 September-October edition of *Transactions of the American Academy of Ophthalmology and Otolaryngology*. These lenses are made from a plastic material, polymethyl methacrylate, which is commonly used to make contact lenses. The lenses are in the shape of a plano convex lens and have a diameter of 5.0 millimeters and a central thickness of from 0.5 millimeters to 0.6 millimeters depending on the required lens strength. In the human eye both lenses are located in front of the pupil near the iris and are anchored by wire loops.

Before inserting a four-loop lens into the eye an intracapsular cataract extraction is performed. The four-loop lenses have one pair of anterior loops formed from 0.15 millimeters Supramid wire lying on the front of the iris and one pair of posterior loops formed from 0.2 millimeters Supramid wire or 0.15 millimeters platina-iridium wire lying just behind the iris. The clearance between the anterior loops and the posterior loops on each side of the lenses is from 0.5 millimeters to 0.75 millimeters. The overall length of the four-loop lens measured from the curved portion of one anterior loop to the curved portion of the other anterior loop is from 7.5 millimeters to 8.0 millimeters and measured from the curved portion of one posterior loop to the curved portion of the other posterior loop is from 8.5 millimeters to 9.0 millimeters. Both the anterior and posterior loops are bent backwards with the loops having a radius of curvature of approximately 30 millimeters. The four-loop lenses clip onto the front and back of the iris diaphragm and the posterior loops and the anterior loops are tied together with suture.

Before inserting a two-loop lens into the eye an extracapsular cataract extraction, which leaves the iridocapsular membrane, is performed. The two-loop lenses are identical to the four-loop lenses with the single exception being that there are no anterior loops. The posterior loops are buried in the iridocapsular membrane.

It is well known that the method of fixing the lens in the eye determines the contact the lens makes with the eye and is decisive to the success of the lens implant. Fixation on the iris diaphragm alone is not a complete fixation because the lens implant, being subject to gravity and centrifugal forces, has a tendency to move about within the eye. Fixation on the rigid iridocapsular membrane diaphragm is a complete fixation. Only the two-loop lens can be affixed to the iridocapsular membrane diaphragm and it is therefore preferred over the four-loop lens.

The present method used to secure the posterior loops on the lenses involves the drilling of four holes adapted to slideably receive the prongs of the posterior loops and disposed perpendicularly to the planar surface of the plano convex lens extending through to the convex surface, the threading of a prong into one of the four holes, the flattening of the end of the prong, and the pulling the flattened end back through the hole thereby enlarging the hole forming a cavity on the convex surface and securing the the flattened end within the hole. The cavities on the convex surface collect organic foreign bodies such as bacteria and inorganic debris in them thereby irritating the eye. In addition the prongs are not as secure as they should be and may become detached from the lens both during the implanting operation or after the lens has been implanted causing serious damage to the eye or they may be pushed out past the convex surface and subject the part of the eye in front of the lens to irritation and possibly to injury.

The prior art lenses can be better understood by reference to FIGS. 1, 2, 3 and 4. Referring to FIG. 1 in which a perspective view of the two-loop lens is shown a two-loop lens 10 has an optical member formed from polymethyl methacrylate and has a convex surface 11 and a planar surface 12. A pair of posterior loops 13, each having prongs 14 fixedly joined to the lens 10. Referring to FIG. 2 in which a top plan view of the two-loop lens 10 is shown the lens 10 has a set of four holes 15 disposed perpendicular to the planar surface 12 and extending through to the convex surface 11. FIG. 3 is a cross-sectional view of the two-loop lens 10 and shows the ends 14a of the prongs 14 flattened and the holes 15 have been enlarged to form cavities 15a and to secure the flattened ends 14a in the holes 15. FIG. 4a shows prong 14 of the posterior loop 13 after it has been inserted into the hole 15 on the side of the planar surface 12 and extending past the convex surface 11. FIG. 4b shows the end 14a of the prong 14 after it has been flattened. FIG. 4c shows the prong 14 after it has been pulled through the hole 15 with its flattened end 14a enlarging the hole 15 to form a cavity 15a on the convex surface 11. This method of securing the posterior loops 13 may be used with loops made from Supramid wire or platina-iridium wire.

SUMMARY OF THE INVENTION

In view of the foregoing factors and considerations characteristic of the prior art it is a primary object of the present invention to provide a prepupillary lens which has its loops for anchoring it in the eye securely in place so that the loops will not become detached either during the implant operation or after the operation.

It is still another object of the present invention to provide a prepupillary lens which eliminates the expensive step of microscopic drilling small holes perpendicular to the planar surface of the lens in order to secure the posterior loops.

It is still yet another object of the present invention to provide a prepupillary lens having a smooth and continuous convex surface without any cavities in which organic foreign bodies such as bacteria or inorganic debris may collect thereby causing irritation to the eye.

It is still another object of the present invention to provide a prepupillary lens which will not subject the portion of the eye in front of the lens to any irritation or injury from the convex surface of the lens or the prongs of the posterior loops protruding therefrom.

In accordance with an embodiment of the present invention, a prepupillary lens to be imparted in a human eye includes a plano convex lens of polymethyl methacrylate having a convex surface and a planar surface into which a pair of posterior loops have their prongs embedded and fused therein. A second embodiment of the invention, also a prepupillary lens to be implanted in a human eye includes the same elements as the first embodiment, and also includes a pair of anterior loops having their prongs inserted in a set of two pairs of parallel bores, disposed in a plane between the planar surface and the convex surface and fused therein.

The features of the present invention will be more readily appreciated as the same becomes better understood by reference to the following detailed description and considered in connection with the accompanying drawings in which reference symbols designate like parts throughout the figures.

DESCRIPTION OF THE DRAWINGS

FIG. 1 is a perspective view of a two-loop lens of the prior art.

FIG. 2 is a top plan view of the two-loop lens of FIG. 1.

FIG. 3 is a cross-sectional view of the two-loop lens of FIG. 1.

FIGS. 4a, 4b and 4c are a series of partial cross-sectional views of the two-loop lens of FIG. 1 depicting the prior art technique of securing the posterior loops in the lenses.

FIG. 5 is a perspective view of the two-loop lens constructed in accordance with the principles of the invention.

FIG. 6 is a cross-sectional view of the two-loop lens of FIG. 5.

FIG. 7 is a schematic drawing of the preferred embodiment after it has been implanted in the human eye.

FIG. 8 is a perspective view of a four-loop lens constructed in accordance with the principles of the invention.

FIG. 9 is a cross-sectional view of the four-loop lens of FIG. 8.

FIG. 10 is a schematic view of the second embodiment of the invention after it has been implanted in the human eye.

DESCRIPTION OF THE PREFERRED EMBODIMENT

Figure 11:
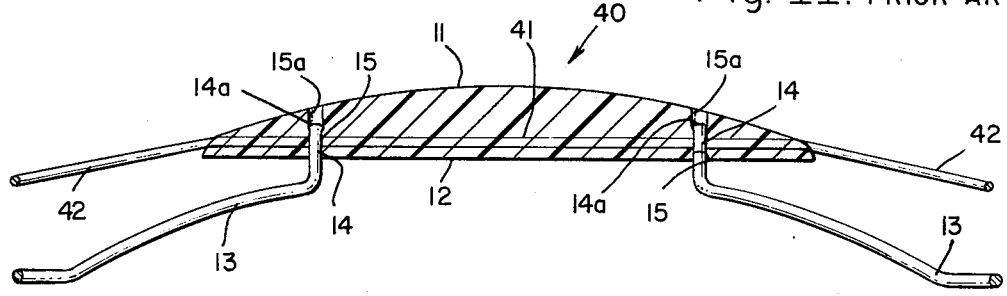
FIG. 11 is a perspective view of a four-loop lens of the prior art.

Briefly, the present invention is an improved prepupillary lens which may be implanted in a human eye. The preferred embodiment of the present invention is a two-loop lens 20, a perspective view of which is shown in FIG. 5. Referring again to FIG. 1, in which a perspective view of the two-loop lens 10 of the prior art is shown, one can see that both lenses 10 and 20 are similar. The lens 20 of the present invention has an optical member formed from a plastic, most commonly polymethyl methacrylate and it has a convex surface 21 and a planar surface 22. The lens 20 also has a pair of posterior loops 23 formed from a platina-iridium wire with the posterior loops 23 having prongs 24 at each end. The lens has a diameter in the range of 4.0 millimeters to 6.0 millimeters and a central thickness in the range of 0.4 millimeters to 0.7 millimeters. The platina-iridium wire has a diameter in the range of 0.10 millimeters to 0.20 millimeters. The dimensions of the preferred embodiment are, respectively, a diameter of 5.0 millimeters, a central thickness between 0.5 millimeters to 0.6 millimeters depending on the required lens strength and a wire diameter of 0.15 millimeters.

Referring now to FIG. 6 the prongs 24 of the posterior loops 23 are embedded in the lens 20 by heating the posterior loops 23 to a temperature in the range of 125° C to 200° C, inserting the heated prongs 24 into the planar surface 22 perpendicularly thereto. The heated prongs 24 melt a small area 25 of the lens 20 thereby distorting the optical properties of this small area 25. The inventors have found that by controlling the temperature of the heated prong 25 they can insure that the diameter of the area 25 is no larger than three times the diameter of the prong 24 which is 0.15 millimeters. When the heated prongs 24 have cooled they are fused in the lens 20.

The inventors used a Unitec electronic bonder to heat the posterior loops 23. The bonder applies a voltage across the posterior loop 23 bringing its temperature to within the specified range. The use of any other device which will heat the posterior loops 23 to a temperature within the specified range is also acceptable for this invention.

Referring now to FIG. 7, which is a schematic drawing of the two-loop lens 20 implanted in a human eye, the lens 20 is placed before the pupil inside the eye. The posterior loops 23 are buried in the iridocapsular membrane. The iridocapsular membrane is rigid and the two-loop lens 20 is anchored securely therein. One should note that the iris of the eye is not connected to the two-loop lens 20 and may function normally. This is one of the advantages of using a two-loop lens; an advantage which was offset by the posterior loops 13 of prior art two-loop lens not being firmly secured to the lens 10. This advantage coupled with the improved technique of securing the posterior loops 23 on the two-loop lens 20 enhances the utility of the present invention.

A second embodiment of the present invention, shown in FIG. 8 as a perspective view of a first four-loop lens 30. Referring to FIG. 8, a four-loop lens 30 formed from polymethyl methacrylate has a convex surface 31 and a planar surface 32. The lens 30 includes a pair of posterior loops 33 formed from platina-iridium wire, each posterior loop 33 having prongs 34 at its end embedded into the planar surface 32 of the lens 30 and a pair of anterior loops 35 formed from Supramid wire, each anterior loop 35 having prongs 36 at its ends embedded into the convex surface 31 of the lens 30 and each anterior loop 35 being aligned with a posterior loop 33. The anterior loops 35 are formed Supramid wire having a diameter in the range of 0.10 millimeters to 0.20 millimeters.

Referring now to FIG. 9, a cross-sectional view of the four-loop lens 30 reveals two sets of pairs of parallel bores 37 which are in a plane disposed between the planes of the planar surface 32 and the convex surfaace 31 of the lens 30, each bore of which extends approximately 1.0 to 1.5 mm into the convex surface 31 of the lens 30 and which are aligned with the posterior loops 33. The prongs 36 of the anterior loops 34 are inserted into the bores 37 of the lens 30. The posterior loops 33 are heated to a temperature within the specified range of 125° C 200° C and the heated prongs 34 are embedded into the planar surface 32 aligned with the bores 37 and fused in the lens 30. An area 38 surrounding the prongs 33 is melted within the lens 30 distorting the optical properties of the area 38, but it has no effect on the optical properties of the lens 30 after it is implanted in the eye. The anterior loops 35 have their prongs 36 inserted into the bores 37 and an electronic bonder applies a heat tack to the planar surface 32 at point 38 adjacent to each bore 37 thereby fusing the prongs 36 of the anterior loops within the lens 30.

Referring to FIG. 10, which is a schematic drawing of four-loop lens 30 implanted in a human eye, the lens is placed inside the eye before the pupil. The posterior loops 33 are placed on the inside of the iris and the anterior loops 35 are placed on the outside of the iris. The posterior loops 33 and the anterior loops are then tied together with sutures.

Figure 12:
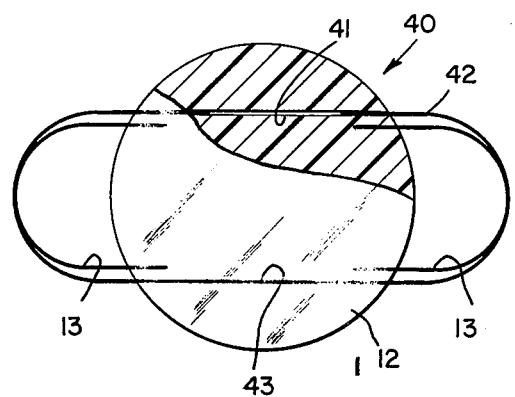
FIG. 12 is a cross-sectional view of the four-loop lens of FIG. 11.

The improved four-loop lens 30 may be compared to a four-loop lens of the prior art, a cross-sectional view of which is shown in FIG. 11 and a partial, cross-sectional view of the four-loop lens' bottom side which is shown in FIG. 12. In FIG. 11 the four-loop lens 40 is seen to be similar to the two-loop lens 10 of the prior art. The four-loop lens 40 also formed from polymethyl methacrylate has a convex surface 11 and a planar surface 12 with a pair of posterior loops 13 formed from 0.2 millimeters Supramid wire and having prongs 14 disposed in a set of holes 15. The posterior loops 13 are secured by flattening the ends 14a of the prongs 14 and pulling the prong through the hole 15 thereby deforming the hole 15 into a cavity and securing the prongs 14 in the hole 15. Reference to FIG. 4 is useful in understanding this prior art technique. The lens 40 also has a pair of parallel bores 41 disposed parallel to the planar surface 12 and aligned with the posterior loops 13. These bores 41 are microscopicly drilled. A 0.15 millimeters Supramid wire forms the anterior loops 42 and is inserted into the bores 41 and its ends are joined with glue 43 therein.

Figure 13:
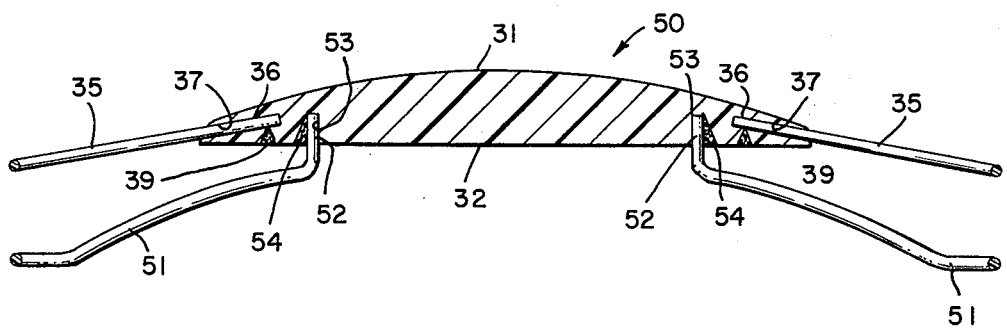
FIG. 13 is a cross-sectional view of another four-loop lens constructed in accordance with the invention.

A third embodiment of the present invention is also a four-loop lens 50, a cross-sectional view of which is shown in FIG. 13. The four-loop lens 50 has a pair of posterior loops 51 formed from 0.2 millimeter Supramid wire having prongs 52 at their ends. The third embodiment of the present invention is similar to the second embodiment with the single exception that the platina-iridium wire has been replaced with a Supramid wire in forming the posterior loops 51. The use of Supramid wire also necessitated that a set of four holes 53 disposed perpendicular to the planar surface 32 and parallel to each other be microscopicly drilled. The prongs 52 of the posterior loops 51 are inserted into these holes 53 and an electronic bonder applies a heat tack to the planar surface at a point 54 adjacent each hole 53 thereby fusing the prongs 52 of the posterior loops 51 within the lens 50.

From the foregoing it can be seen that both an improved two-loop lens and an improved four-loop lens have been provided which has an anchor for holding a prepupillary lens implanted in a human eye that is more secure than the anchors used in the prior art. The anchors comprise a pair of posterior loops which are embedded into the lens and fused therein and, in the case of the four-loop lens, a pair of anterior loops inserted into bores in the lens and fused therein. Additionally it has been noted that by embedding the posterior loops into the lens the inventors have eliminated cavities on the convex surface of the lens which were formed on the lens when the prior art technique was used to secure the posterior loops. Furthermore it should be noted that the sketches are not drawn to scale and that thickness and distances of and between various figures are not to be considered significant.

Accordingly it is intended that the foregoing disclosure and showing made in the drawing shall be considered only as an illustration of the principles of the invention. The invention will be set out with particularity in the appended claims.

What we claim:

1. A prepupillary lens which is to implanted into a human eye, comprising:
    a plastic member in the shape of a plano convex lens having a planar surface and a convex surface; and
    b. a pair of posterior loops, each having a pair of prongs embedded into said planar surface of said plastic member and fused by heat therein so that each prong of said pairs of prongs does not extend through to said convex surface of said plastic member and so that each prong of said pairs of prongs is surrounded by a melted area, the diameter of which is less than three times the diameter of said each prong.

2. The prepupillary lens according to claim 1 wherein said plastic member is formed from polymethyl methacrylate and has a diameter in the range of 4.0 millimeters to 6.0 millimeters and a central thickness in the range of 0.4 millimeters to 0.7 millimeters.

3. The prepupillary lens according to claim 2 wherein said posterior loops are formed from platina-iridium wire having a diameter in the range of 0.10 millimeters to 0.20 millimeters, said posterior loops, having been heated to a temperature in the range of 125° C to 200° C and embedded into said planar surface of said plastic member.

4. The prepupillary lens according to claim 3 wherein said plastic member has a set of two pairs of parallel bores disposed between said planar surface and said convex surface, and also comprising:
    a. a pair of anterior loops formed from Supramid wire having a diameter in the range of 0.10 millimeters to 0.25 millimeters having prongs which are disposed in said bores and fused therein.

5. The prepupillary lens according to claim 2 wherein a set of four holes disposed perpendicular to said planar surface and not extended through to said convex surface and wherein said posterior loops are formed from Supramid wire having a diameter in the range of 0.15 millimeters to 0.25 millimeters with said prongs of posterior loops inserted in said holes and fused therein.

6. The prepupillary lens according to claim 5 wherein said plastic member has a set of two pairs of parallel bores disposed between said planar surface and said convex surface, and also comprising:
    a. a pair of anterior loops formed from Supramid wire having a diameter in the range of 0.10 millimeters to 0.20 millimeters having prongs which are disposed in said bores and fused therein.

* * * * *